United States Patent [19]

Pinto

[11] 4,455,394

[45] Jun. 19, 1984

[54] METHANOL PRODUCTION

[75] Inventor: Alwyn Pinto, Linthorpe, England

[73] Assignee: Imperial Chemical Industries Limited, London, England

[21] Appl. No.: 430,674

[22] Filed: Sep. 30, 1982

Related U.S. Application Data

[63] Continuation of Ser. No. 263,732, May 14, 1981, abandoned.

[30] Foreign Application Priority Data

May 20, 1980 [GB] United Kingdom ................ 8016619

[51] Int. Cl.³ ...................... C07C 27/06; C07C 31/04
[52] U.S. Cl. .................................... 518/704; 518/702; 518/703; 518/705
[58] Field of Search .............. 518/702, 703, 704, 705, 518/712, 713

[56] References Cited

U.S. PATENT DOCUMENTS 3,064,029 11/1962 White.
3,763,205 10/1973 Green.
3,920,717 11/1975 Marion.
4,072,625 2/1978 Pinto.

OTHER PUBLICATIONS

Quartulli, Hydrocarbon Processing, 1975, pp. 94–99.

Primary Examiner—Howard T. Mars
Attorney, Agent, or Firm—Cushman, Darby & Cushman

[57] ABSTRACT

In a methanol production process comprising synthesis gas generation, catalytic synthesis, recovery of crude methanol and purification by distillation, organic compounds of higher boiling point than methanol (the so-called "fusel oil" stream) are contacted in liquid form with a gaseous stream to be fed to synthesis gas generation, whereby to convert those compounds to synthesis gas. When an alkali is added to the crude methanol before distillation the contacting step permits utilisation of the organic compounds in the fusel oil, leaving an alkali compounds solution, which is withdrawn.

8 Claims, 1 Drawing Figure

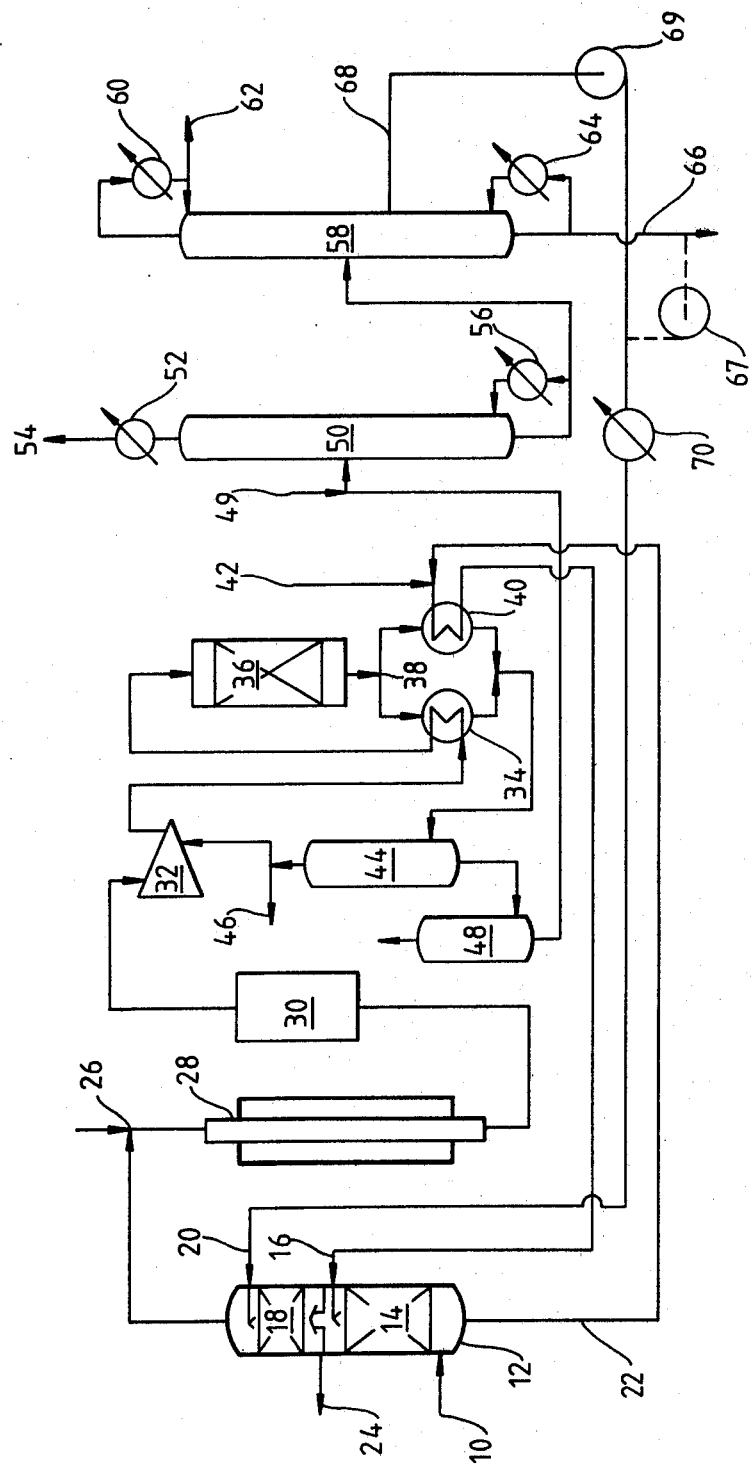

METHANOL PRODUCTION

This is a continuation of application Ser. No. 263,732 filed May 14, 1981, now abandoned.

This invention relates to methanol production and in particular to a process involving a step by which the efficiency of conversion of a carbonaceous feedstock to methanol is improved.

Over the last decade considerable effort has been devoted to increasing this efficiency, by designing processes with improved energy recovery or by avoiding losses of material. From some by-product streams, however, it is very difficult to recover pure methanol because of their content of impurities and therefore they have been either discarded or burnt as fuel. One of these is the so-called "fusel oil" stream from distillative methanol purification, which cannot be re-cycle as a whole to any catalytic step in synthesis gas generation or synthesis because of its content of alkali, which is added to the distillation feed to neutralise acid impurities. This fraction can amount to a few percent of the carbon in the feedstock to the process and thus it would be very desirable to recover it.

We have now devised a convenient process by which such a fraction can be recovered and converted to methanol.

In this specification the expression "fusel oil" denotes organic compounds having a higher boiling point than methanol $CH_3OH$ and formed as by-products during catalytic methanol synthesis. The expression originally denoted organic compounds of higher boiling point than ethanol $C_2H_5OH$ formed during fermentation, but that meaning is inapplicable here.

According to the invention a methanol production process comprises the steps
 (a) generating methanol synthesis gas by reaction of a carbonaceous feedstock with a gasifying agent selected from steam, carbon dioxide and oxygen;
 (b) reacting the synthesis gas over a methanol synthesis catalyst and recovering a crude methanol liquid product from the reacted gas;
 (c) distilling the crude liquid product and separating therefrom a purified methanol stream and a fusel oil stream containing organic compounds of higher boiling point than methanol;
and is characterised by contacting the fusel oil stream in liquid form with a gaseous stream to be subjected to chemical reaction within step (a), whereby to convert organic compounds contained in the fusel oil stream to methanol synthesis gas.

In methanol synthesis gas generation the reaction of a carbonaceous feedstock, such as natural gas, refinery off-gas, gaseous hydrocarbons, light petroleum distillate, heavier vaporisable hydrocarbons, non-vaporisable hydrocarbons, coal or coke, takes place typically at over 700° C. and the temperature may be as high as 1100° C. for a catalytic process, still higher for a non-catalytic process, in order to effect sufficiently complete reaction to crude synthesis gas containing carbon oxides and hydrogen. If the feedstock is one of the first 4 mentioned the reaction is most often carried out without oxygen over a catalyst in tubes externally heated in a furnace ("steam reforming") but can be carried out in an insulated vessel if oxygen is also fed ("partial oxidation") or if adequate preheating is effected. A step of partial oxidation using air is applied to the product of such a reaction if methanol production is integrated with ammonia production. If the feedstock is one of the last 4, the reaction is usually carried out in the presence of oxygen without a catalyst. Depending on the hydrogen-to-carbon-ratio of the carbonaceous feedstock and on the extent to which oxygen is used, synthesis gas generation may involve a CO-shift and $CO_2$-removal stage to bring the hydrogen to carbon oxides ratio to the level required for methanol synthesis. The crude synthesis gas is cooled and sufficiently freed of unreacted steam before passing it to the synthesis section.

Synthesis gas generation may alternatively begin with the shift reaction of carbon monoxide with steam to give carbon dioxide and hydrogen (outlet temperature over 250° C.) and $CO_2$-removal, if carbon monoxide is available as a starting material.

The fusel oil stream in liquid form can be contacted with any of the streams fed to these synthesis gas generation processes but naturally the fed stream is preferably one that does not support combustion. Most conveniently the fed stream is hydrocarbon or carbon monoxide or steam or a mixture thereof, especially a gaseous or vaporised hydrocarbon to be fed to synthesis gas generation by catalytic reaction with steam. Preferably such hydrocarbon has been humidified with hot water.

The pressure in the synthesis gas generation section is typically up to 100 and typically in the range 10–50 atm abs. and thus the gas usually has to be compressed before feeding it to the methanol synthesis.

In order to economise in energy consumption, preferably steam is generated by heat exchange with the crude synthesis gas stream and also the flue gas of the furnace if a steam reforming process is used. The steam pressure is preferably in the range 50–120 ata, as a result of which it is practicable to let it down in an engine of the pass-out type and to use the exhaust steam as the feed for synthesis gas generation, directly or via a humidifier as disclosed in our published UK application No. 2027737. The engine may drive the synthesis gas compressor directly or may drive an electric generator powering the compressor. In favourable conditions enough steam can be generated to provide, directly or indirectly, the mechanical power required in other parts of the process, such as the synthesis gas circulator (if a recycle process is used) and various feed-pumps and fans. Part of the steam can be used in condensing engines or in engines exhausting at less than synthesis gas generation pressure, for example into the re-boilers of the methanol distillation to be described.

The pressure at which methanol is synthesised in step (b) is typically in the range 10–400 atm abs. This range includes older-type processes using a zinc-chromite catalyst in which the pressure is in the range 150–400 atm abs. and the temperature in the range 300°–450° C. Preferably the synthesis is of the newer type using a copper-containing catalyst and the presure is under 150, especially in the range 30–120 atm abs. For such a process the catalyst outlet temperature is typically in the range 160°–300° C., especially 190°–280° C. Whereas the fusel oil stream in the older-type processes amounts typically to 0.5 to 4.0% by weight of the total refined methanol product, it amounts to only 0.5 to 2.0% in the copper-catalysed process. Nevertheless, in view of the generally better energy economy of the copper-catalysed process the recovery of its small fusel oil stream is worthwhile.

The copper-containing catalyst preferably contain also one or more difficulty reducible oxides. These usually include zinc oxide and there may also be present silver or an oxide of one or more of boron, magnesium, aluminium, vanadium, chromium, manganese, zirconium, rare earths or actinides. Particularly useful catalysts contain alumina, as described in our UK Pat. No. 1159035, or a spinel as described in our UK Pat. No. 1296212.

A variety of general types of methanol synthesis process have been proposed, differing in the methods adopted for handling the heat evolved in the synthesis reaction. Thus synthesis may be over a catalyst in tubes surrounded by a coolant or in the space around tubes containing coolant. The coolant may be for example pressurised water or a mixture of diphenyl and diphenyl ether; the pressurised water can be used as feed for high pressure steam generation or, like the mixture, heat-exchanged in liquid form with such water. More conveniently the hot water can be directly heat exchanged with a gaseous or vaporised feed to synthesis gas generation to effect humidification, preferably before contact with the fusel oil stream, and then need not be purified to boiler feed standards. Alternatively such coolant water may be allowed to boil and the resulting intermediate pressure steam condensed in heat exchange with the water to be fed to high pressure steam generation or the direct heat exchange. In another process the catalyst bed can be in several parts with heat-abstraction by coolant between the parts. In a third process the catalyst temperature can be controlled by heat exchange with cool feed gas passing through tubes in the catalyst bed or through the space surrounding catalyst-filled tubes. For the first two of such processes reactors not much simpler than previously proposed steam raising processes are required, however, and it may therefore be preferred to use the third or, better still, a process in which the temperature is controlled by injecting cool synthesis gas ("quench gas") into the hot reacting synthesis gas. Quench gas can be injected into mixing chambers between successive parts of a catalyst bed or successive reactor vessels. A very convenient system involves a single body of catalyst in which are disposed catalyst-free perforated hollow bars each having a sparger for introducing the quench gas, the bars being large enough in cross section for their interiors to constitute mixing zones and close enough together or to the catalyst bed walls to cause a substantial proportion of reaction mixture to pass through their interiors, as described in our UK specification No. 1105614. The temperature of quench gas can be below 50° C., but thermal efficiency is better if it is at between 50° and 150° C.

Using the preferred copper-containing catalyst the volume space velocity of the flow of gas through the catalyst bed is typically in the range 5000–50000 hour$^{-1}$ and is preferably fixed at a level such that the gas leaves the catalyst bed when the quantity of methanol formed has been sufficient to raise the gas temperature to the design level, which is under 300° C. and most preferably under 280° C. The methanol content of the reacted gas is for example 2–5% for a process at 50 atm abs. and proportionately more at higher pressures. Consequently unreacted carbon oxides and hydrogen are left over after methanol has been recovered and are preferably passed again over a methanol synthesis catalyst, for example, by recirculation to the inlet of the catalyst and mixing with fresh synthesis gas. The above space velocity range refers to the mixture in such a process.

In a preferred way of transferring to the water the heat evolved in the synthesis, reacted gas leaving the catalyst is passed through two parallel heat exchanges, the first of which heats synthesis gas to synthesis inlet temperature, which is preferably 20°–40° C. lower than the outlet temperature of the catalyst bed. The second heats water to a temperature preferably in the range 150°–260° C. under a pressure too high to permit boiling to take place or heats a coolant (such as described above) from which heat is to be transferred to such water. The reacted gas becomes cooled initially to 150°–190° C. in these exchangers. Preferably it is then (suitably after re-uniting the two streams) heat-exchanged with cold synthesis gas from the generation section or methanol recovery or both. This affords a useful secondary heat recovery and decreases the capacity required of the first heat exchanger. After secondary heat recovery the gas is passed to a cooler and separator for recovery of methanol.

In the alternative way of transferring heat to the water, by raising steam in the reactor and condensing it in heat exchange with the water, the reacted gas leaving the reactor can be cooled to 50°–150° C. in a single heat exchange with cold synthesis gas and then passed to the cooler and separator.

Unreacted gas from the separator is preferably recirculated but, if the fresh synthesis gas has a hydrogen to carbon oxides ratio different from stoichiometric and/or contains non-reactive gases such as nitrogen, methane or argon, it is necessary to purge a part of it in order to prevent the concentration of such gases from building up too much in the gas passing over the catalyst. Since the purge gas is at only slightly under synthesis pressure, a useful energy recovery results from letting it down in an expansion engine. Since the purge gas is at the low temperature of methanol separation, it is capable of absorbing low-grade heat from other process streams in the plant and thus the energy recovery from purge gas is yet more valuable. After letting-down, the purge gas can be used as a fuel or source of hydrogen for purposes such as feedstock desulphurisation or a fuel cell.

Crude liquid methanol in the separator at synthesis pressure is run off into a let-down vessel and there the pressure is decreased to atmospheric pressure or slightly higher. This permits volatiles, principally dimethyl ether, carbon dioxide and methane to boil off. They amount typically to 1 to 5 mol % of the total synthesis product and are worth recovering by recycle to the inlet of synthesis gas generation or as fuel.

The resulting crude methanol is then subjected to purification by distillation. Since it contains traces of organic acids it is first neutralised by adding a base, such as an alkali metal hydroxide or carbonate, an amine or an ammonium hydroxide. A typical base addition is 40 to 120 ppm w/w calculated as stoichiometrically equivalent NaOH for high temperature process methanol or 20 to 100 ppm w/w for methanol synthesised over a copper containing catalyst at under 300° C. The direct contact with the stream to be fed to synthesis gas generation in step (a) is in conditions preferably effecting incomplete evaporation of the fusel oil stream and a solution of alkali metal compounds is withdrawn.

The invention can include any distillation system that produces a "fusel oil" stream. It is especially advantageous when that stream is liquid taken from a column fed with the crude methanol from the let-down vessel or with the bottoms liquid from a column fed with such crude methanol, the off-take point being at a level below the feed level. Alternatively or additionally the fusel oil stream can be taken from a level above the feed level in such a column or can be the compounds of limited solubility in water which are recovered from the overhead of a water-extractive distillation column. Whereas it has been proposed to separate the higher alcohol from methanol in such streams by relying on their low solubility in water, this is unnecessary in the process of the invention because the whole organic content of such streams can be returned to the process in a single operation.

The following are examples of distillation systems that can be used:

1. Single column, with volatiles taken overhead, product methanol at a high level, fusel oil as vapour above the feed and/or as liquid below the feed and water as bottoms;
2. Two columns, the first a "topping column" from which volatiles are taken overhead and aqueous methanol as bottoms, and the second a "rectifying column" from which product methanol is taken overhead or at a high level and water as bottoms. At least the rectifying column includes an off-take for fusel oil as vapour above the feed and/or as liquid below the feed;
3. Two columns, the first of which is a water-extractive column in which there is a feed of water at a level above the crude methanol feed level, sufficient to produce a bottoms liquid containing over 40, for example 40-60 or even 80-95% w/w of water. (The effect of water is to increase the relative volatility of impurities such as ketones and higher alcohols so that they pass out overhead with the volatiles and thus provide a fusel oil stream). This column may include one or more direct fusel oil side off-takes. The second column is similar to the rectifying column of system 2;
4. Systems in which a semi-crude aqueous methanol is taken as liquid above the feed in such a single column or rectifying column and passed to a final rectifying column, from which product methanol is taken overhead or at a high level (to storage or as additional reflux to the preceding column) and water or aqueous methanol is taken as bottoms. If a side stream rich in ethanol and higher alcohols is taken it can be returned to synthesis gas generation according to the invention;
5. Systems in which higher boiling components are removed from methanol by adsorption: here a fusel oil stream is obtained by regenerating the adsorbent;
6. Systems in which a stream containing methanol and higher boiling compounds is separated by distillation in a separate column or is returned to a main column so as to make possible a methanol-depleted fusel oil offtake.

Since the fusel oil stream is returned to the process, it is unnecessary to design the distillation columns so as to limit its magnitude or its methanol content to the low levels normally applicable.

The fusel oil stream, whether or not depleted in methanol, is heated under sufficient pressure to keep it in the liquid state, to a temperature preferably in the range 150°–250° C., suitably by heat exchange with reacted synthesis gas or condensing steam, and then fed to the zone in which it contacts a gaseous feed to the synthesis gas generation step. Very conveniently the gaseous feed is a mixture of hydrocarbon feedstock and steam, especially as obtained by direct heat exchange of hydrocarbon with water heated by reacted synthesis gas. The temperature and pressure in the contacting zone are chosen so as to keep the fusel oil stream in the liquid state and to avoid complete evaporation of its content of water, since this would cause deposition of the alkali or amine salts dissolved in it. If desired, additional water can be mixed into the fusel oil stream as taken from the distillation column.

One preferred form of the invention is shown in the accompanying drawing, which is a flow diagram of a process for producing methanol from natural gas.

Desulphurised warm natural gas is fed at 10 to the bottom of two-stage packed tower 12. In the bottom section of tower 12 it passes up through packing 14 in counter current contact with hot water fed in at 16 from a source to be described. The resulting humidified gas passes through a chimney plate into the upper section of tower 12 in which it contacts a fusel oil stream, possibly with added water, fed in at 20 from the methanol purification step to be described and strips from it substantially its whole content of organic compounds. From tower 12 a water stream is taken by line 22 leading to a water heater and a waste solution of sodium salts in water is taken by line 24 leading to a drain. The overhead stream from tower 12, consisting of natural gas, steam, methanol vapour and higher alcohol vapours is mixed at 26 with more steam and the mixture is fed via a preheater (not shown) to a steam reforming catalyst in externally heated tubes 28. The resulting gas, containing carbon oxides, hydrogen, methane and excess steam is passed through item 30, which represents generally a heat recovery, cooling, steam condensation and water removal system as in common use. The dried cool gas is compressed to synthesis pressure and mixed with recycled unreacted gas in compressor 32. The mixture is heated to synthesis catalyst inlet temperature in heat exchanger 34 and passed into synthesis reactor 36. (In practice more than one stage of heat exchange would be used and a portion of the gas might be fed to reactor 36 as a quench stream without or with less heating. Other practicable processes include a synthesis reactor with temperature control by indirect heat exchange instead of by quenching). The hot reacted gas leaving reactor 36 is divided at 38 into a preheat stream, which is fed through the hot side of heat exchanger 34, and a heat recovery stream; this stream is passed through the hot side of heat exchanger 40, which receives recycled water from line 22, fresh water from line 42 and provides the hot water required at 16 to humidify natural gas in tower 12. After heat exchangers 34 and 40 the cooled reacted gas streams are re-united, cooled further in minor heat exchangers (not shown) to below the dewpoint of methanol and passed into catchpot 44, where methanol and water separate as liquid and from which an unreacted gas stream is taken overhead, partly purged at 46 and fed to compressor 32 as the recycled unreacted gas stream. The gas purged at 46 can be let down in a turbine, preferably after heat exchange with reacted methanol synthesis gas.

The bottoms liquid stream from catchpot 44 is passed into let-down vessel 48, in which dissolved gases boil off, and then led via alkali addition point 49 to a middle plate of topping column 50. In column 50 methanol and components more volatile then methanol are taken overhead. Methanol is condensed in cooler 52 and passed back as reflux. Volatiles, chiefly dimethyl ether, are taken off at 54 and used as process feed or fuel for steam reforming tubes 28. Methanol and water leave column 50 as bottoms, are partly returned by steam-heated re-boiler 56 and for the rest are passed to a middle plate of rectifying column 58. At the head of column 58 methanol vapour is condensed at 60 and partly refluxed, partly taken as product at 62. The bottoms liquid of column 58, a weak aqueous alkali salt solution, is partly recycled via re-boiler 64, partly run to waste at 66: if desired this stream could be used (following the dotted path, for example, via pump 67) in a humidifier such as the upper section of tower 12, provided a purge is maintained, but it is not suitable for use as boiler feed water. Column 58 includes also liquid purge off-take 68, which is below the level of the feed and consequently includes water and alkali metal salts as well as methanol and higher boiling organic compounds. There may be a region of relatively constant methanol-to-water ratio between the feed plate and purge off-take 68 as the result of upwardly misplaced feed, which has the effect of decreasing the methanol content of the purged liquid. The purged liquid is fed by pump 69, at the outlet of which it is under a pressure high enough to prevent boiling, to heater 70 and thence to packed tower 12 at point 20 whereby its content of organic compounds is added to the process feedstock.

EXAMPLE

In a typical process using this flowsheet the process conditions and flow-rates are as shown in Table 1, compositions as shown in Table 2.

TABLE 1

| Position | Stream | Flow rate kg. mol h$^{-1}$ | Temperature °C. | Pressure bar abs. |
| --- | --- | --- | --- | --- |
| 10 | methane | 2000 | 120 | 26 |
| 16 | water | 13750 | 200 | 26 |
| entering 18 (gas) | methane steam | 2000 1623 | 185 | 26 |
| 20 | fuel oil | 52.2 | 185 | 26 |
| 24 | waste | 39.02 | 185 | 26 |
| 12 top | steam + gas | 3636.18 | 185 | 26 |

TABLE 2

| | Composition % molar | | | |
| --- | --- | --- | --- | --- |
| Stream | CH$_3$OH | Higher alc. as C$_2$H$_5$OH | H$_2$O | CH$_4$ |
| Fuel oil 20 | 53.0 | 1.0 | 46.0 | — |
| Waste 24 | — | — | 99.97 | 0.02 |
| Steam + gas (12 top) | 0.76 | 0.01 | 44.22 | 55.01 |

I claim:
1. A methanol production process comprising the steps
   (a) generating methanol synthesis gas by catalytic reaction with steam of a gaseous or vaporized hydrocarbon;
   (b) reacting the synthesis gas over a methanol synthesis catalyst and recovering a crude methanol liquid product from the reacted gas;
   (c) adding alkali to the crude liquid product, distilling the resulting admixture and separating therefrom a purified methanol stream and a liquid fuel oil stream containing said alkali and organic compounds of higher boiling point than methanol; and
   (d) feeding said fuel oil stream in the liquid state to a zone where it is contacted by said gaseous or vaporized hydrocarbon under conditions effecting incomplete evaporation of the fuel oil stream; separating organic compounds from the fuel oil with said hydrocarbon, leaving a liquid waste solution containing said alkali; feeding said mixture of organic compounds and said hydrocarbon to step (a) and separating said liquid waste solution.

2. The process of claim 1 in which said hydrocarbon is humidified before contacting it with the fuel oil stream.

3. The process of claim 1 in which the fuel oil stream is heated to a temperature in the range of 150°–250° C. under sufficient pressure to keep it in the liquid state, before contacting it with the hydrocarbon to be subjected to chemical reaction in step (a).

4. The process of claim 1 in which methanol synthesis in step (b) is over a copper-containing catalyst at an outlet temperature in the range 190°–280° C. and the fuel oil stream amounts to 0.5 to 2% by weight of the total refined methanol product.

5. The process of claim 2 in which the humidification is effected by means of hot water, said hot water being heated by the heat evolved in methanol synthesis over a copper-containing catalyst at an outlet temperature in the range of 190°–280° C.

6. The process of claim 1 in which volatile compounds evolved from the crude methanol before and during distillation are recycled to the inlet of synthesis gas generation.

7. In a methanol production process comprising the steps
   (a) generating methanol synthesis gas by catalytic reaction with steam of a gaseous or vaporizable hydrocarbon,
   (b) reacting the synthesis gas over a copper-containing methanol synthesis catalyst at an outlet temperature in the range of 190°–280° C. and recovering a crude methanol liquid product from the reacted gas;
   (c) adding alkali to the crude liquid product, distilling the resulting admixture and separating therefrom a purified methanol stream and liquid fuel oil stream containing said alkali and organic compounds of higher boiling point than methanol;
   (d) recovering heat evolved in said methanol synthesis by producing hot water and using said hot water to humidify the gaseous or vaporizable hydrocarbon fed to step (a) whereby to provide part of the steam requirement of step (a);
   the improvement, resulting in conversion to methanol synthesis gas of organic compounds contained in said fuel oil stream in step (a) while avoiding contact with the catalyst in step (a) of alkali in said fuel oil stream, comprising feeding said fuel oil stream, at a temperature in the range of 150°–250° C. under sufficient pressure to keep said stream in the liquid state, to a zone where said stream is contacted with the humidified gaseous or vaporized hydrocarbon produced in step (d) under conditions effecting incomplete evaporation of said stream, separating organic compounds from said stream with said humidified gaseous or vaporized hydrocarbon, leaving a liquid waste solution containing said alkali, feeding the mixture of said organic compounds and humidified hydrocarbon to step (a) and separating said liquid waste solution.

8. In a methanol production process comprising
   (a) generating methanol synthesis gas by reaction of a carbonaceous feedstock with a gasifying agent selected from steam, carbon dioxide and oxygen;

(b) reacting the synthesis gas over a methanol synthesis catalyst and recovering a crude methanol liquid product from the reacted gas;
(c) adding alkali to the crude liquid product, distilling the resulting admixture and separating therefrom a purified methanol stream and a liquid fusel oil stream containing said alkali and organic compounds of higher boiling point than methanol; and
(d) recovering feedstock value in said fusel oil stream by feeding it to step (a);
the improvement whereby the resulting alkali content of the fusel oil is prevented from entering synthesis gas generation, said improvement comprising contacting said fusel oil stream in the liquid state with a gas to be fed to said synthesis gas generation and selected from the group consisting of said carbonaceous feedstock if gaseous or vaporized and said gasifying agents under conditions effecting incomplete evaporation of the fusel oil stream; separating organic compounds from the fusel oil with said gas, leaving a liquid waste solution containing said alkali; feeding said mixture of organic compounds and gas to step (a) and separating said liquid waste solution.

* * * * *